United States Patent [19]

Johnson

[11] 4,317,369

[45] * Mar. 2, 1982

[54] ULTRASOUND IMAGING APPARATUS AND METHOD

[75] Inventor: Steven A. Johnson, Preston, Id.

[73] Assignee: University of Utah, Salt Lake City, Utah

[ * ] Notice: The portion of the term of this patent subsequent to Sep. 2, 1997, has been disclaimed.

[21] Appl. No.: 147,990

[22] Filed: May 8, 1980

Related U.S. Application Data

[63] Continuation-in-part of Ser. No. 942,740, Sep. 14, 1978, Pat. No. 4,222,274.

[51] Int. Cl.$^3$ .......................................... G01N 29/00
[52] U.S. Cl. .................................................... 73/607
[58] Field of Search ................ 73/607, 626, 596, 599, 73/600, 602, 606, 609, 618; 128/660; 367/105

[56] References Cited

U.S. PATENT DOCUMENTS

| | | | |
|---|---|---|---|
| 3,805,596 | 4/1974 | Klahr | 73/602 |
| 3,885,224 | 5/1975 | Klahr | 73/602 |
| 4,047,520 | 9/1977 | Soldner et al. | 73/620 |
| 4,074,564 | 2/1978 | Andersen | 73/596 |
| 4,075,883 | 2/1978 | Glover | 73/602 |
| 4,100,916 | 7/1978 | King | 128/660 |
| 4,105,018 | 8/1978 | Greenleaf et al. | 128/660 |
| 4,109,642 | 8/1978 | Reid et al. | 73/622 |
| 4,109,644 | 8/1978 | Kojima | 128/660 |
| 4,120,291 | 10/1978 | Paton et al. | 73/618 |

OTHER PUBLICATIONS

S. A. Johnson et al., *Quantitative Synthetic Aperture Reflection Imaging Correction for Refraction and Attenuation: Appl. Seismic Tech. in Medicine*, pp. 337-348, Feb. 1978.
S. A. Johnson et al., *High Resolution Ultrasound Echo and Reconstruction Imaging from Temporal and Spatial Projections by Adaptive Ray Tracing*, pp. 1-5, Feb. 1978.
S. A. Johnson et al., *Ultrasound Images Corrected for Refraction and Attenuation: Comparison of High Resolution Methods*, pp. 55-71, Aug. 1978.
S. A. Johnson, et al., "Algebraic and Anly. Inversion Acou. Data Partially or Fully Enclosing Apertures", *Acoustical Imaging*, pp. 1-22, Jun. 1978.

Primary Examiner—Stephen A. Kreitman
Attorney, Agent, or Firm—H. Ross Workman; J. Winslow Young; Allen R. Jensen

[57] ABSTRACT

A ring of transmitter and receiver transducer arrays circumscribes an object to be scanned. Semicircular wave fronts of ultrasound energy are propagated from different points around the ring of transducers by triggering the transmitter arrays in sequence. The reflected and transmitted ultrasound energy picked up by the receiver arrays is then electronically analyzed and a synthetically focused image corresponding to the scanned object is reconstructed on a display screen. Surprisingly high quality resolution for the reconstructed images is achieved by carefully controlling the type of waveform from which the displayed image is reconstructed. In one embodiment of the invention, the signals received by the receiver arrays are processed by a waveshaping circuit to achieve the desired waveform. In a second embodiment of the invention, the desired waveform is generated by a waveform generator circuit and transmitted by the transmitter arrays. The quality of resolution for the reconstructed image of reflection is further improved by obtaining, through a computer aided ray tracing technique, the connecting rays between each point in the object and each transmitter and receiver array element. Data sampling times for each point in the reconstructed image may then be corrected for refraction by computer aided integration of the object's refractive index along each connecting ray. Correction of the sampled data for amplitude attenuation is similarly obtained by computer aided integration of the object's linear attenuation coefficient along the connecting rays.

4 Claims, 23 Drawing Figures

ULTRASOUND IMAGING APPARATUS AND METHOD

This application is a continuation-in-part of my co-pending application Ser. No. 942,740, filed Sept. 14, 1978, now U.S. Pat. No. 4,222,274.

BACKGROUND

1. Field of the Invention

The present invention relates to an apparatus and method for ultrasound imaging of biological tissue according to the impulse-echo technique, and more particularly the present invention relates to a novel and unobvious apparatus and method for reconstructing images of reflection in biological tissue or other media using synthetically focused ultrasound energy.

2. The Prior Art

It has long been known that ultrasonic or acoustic waves in the frequency range of 15,000 cycles per second and higher can be propagated through many solids and liquids. Ultrasound waves are usually considered to be those in the frequency range from approximately 50,000 cycles per second to 10,000,000 cycles per second and higher. Ultrasound energy waves are partially reflected and partially transmitted at any interface between two media of different density. The product of material density and sonic wave velocity is known as the acoustic impedance, and the amount of reflection which occurs at the interface between two media is dependent upon the amount of change in the acoustic impedance between one medium as opposed to the other medium.

These principles have long been used for imaging reflecting bodies within an ultrasound propagation medium. For example, the organs of a human body as well as bones and sinew act as reflecting bodies within the soft tissue of the body. Likewise, any foreign inclusion will act as a reflecting body. Thus, noninvasive internal examination and medical diagnosis of the human body by ultrasound imaging has long been known in the art. For example, piston type transducers have been used for over 30 years to image some parts of the body.

The inherent advantages of noninvasive medical diagnosis by ultrasound imaging are readily apparent. Unlike exploratory surgery or x-rays, ultrasound imaging permits internal examination of an organ without damaging the surrounding tissue and organs of the body and with much less trauma to the patient.

However, despite the many advantages which may be derived from noninvasive examination by ultrasound imaging, in the past ultrasound imaging has been somewhat limited in its application. One of the primary problems encountered in this regard is the difficulty in providing reflection images of high quality resolution. These images may often be blurred or distorted to some degree, making accurate diagnosis difficult, particularly with respect to very small objects in the body.

Thus, recently much attention has been directed to improving the quality of resolution of ultrasound images. For example, linear phased (or so-called "beam steering") transducer arrays have demonstrated improved depth of focus and time resolution. See, for example, Somer, J. C., W. A. Oosterbaan and H. J. Freund: *Ultrasonic Tomographic Imaging of the Brain with an Electronic Sector Scanning System*, Proceedings of the 1973 IEEE Ultrasonic Symposium, Nov. 5-7, 1973, and Thurstone, F. L., and O. T. Van Ramm: *A New Ultrasound Imaging System Employing Two-Dimensional Electronic Beam Steering*, Heart Bulletin, Volume 4, p. 51 (1973). It has also been demonstrated that non-straight line transducer array configurations may be employed to enhance resolution quality in ultrasound images by increasing the aperture for transmitting and receiving ultrasound energy. See, for example, Maginness, M. G., J. D. Plummer and J. D. Meindl: *A Cardiac Dynamics Visualization System*, Proceedings of the 1973 IEEE Ultrasonic Symposium, Nov. 5-7, 1973; and Green, P. S., L. F. Schaefer, E. D. Jones and J. R. Suarez: *A New High-Performance Ultrasonic Camera System*, Fifth International Symposium on Acoustical Holography Imaging, July 18-20, 1973. These improvements in the resolution quality of ultrasound images increase the ability of a system to detect small, focal lesions such as cancer, abscesses, or infarcts of less than one centimeter in diameter.

However, often more fundamental than the focal lesion itself, regardless of its size, is the state of the tissue surrounding the lesion. The pattern of the adjacent tissue plays a crucial role in the identification of specific diseases by supplying the physician with information concerning the local context of the bodily processes which are resulting in the lesion.

Compared to tumor nodules and the like, the structures of the surrounding normal tissue are relatively delicate. The tissue structure is essentially determined by the dimensions of the fibrous and vascular framework of an organ and is responsive to the pathologic processes.

It would therefore be highly desirable to be able to image such delicate patterns as those associated with, for example, the interstitial spaces of parenchymal organs, or the tertiary branching of major arteries of the heart, brain, kidneys and lungs, or the biliary ducts of the liver and the ductular system of the breast and pancreas. However, ultrasound imaging of these delicate tissues requires a resolution capability not presently possible with commercially known ultrasound scanning systems.

Accordingly, what is needed is an improved ultrasound imaging apparatus and method capable of high quality resolution for images of reflection for highly delicate tissue and the like. Such a device would provide a significant advancement in the state of the art by providing noninvasive diagnostic techniques through ultrasound imaging which could be used for pathogenesis, prevention and early detection of disease rather than being limited to the diagnosis of gross advanced lesions. Such an invention is disclosed and claimed herein.

BRIEF DESCRIPTION AND OBJECTS OF THE INVENTION

The ultrasound imaging apparatus and method of the present invention provides high quality resolution real time images of reflection by synthetically focusing ultrasound energy. Novel structure and method are provided for sending and receiving ultrasound energy waves and for reconstructing the images of reflection from an arbitrary waveform selected to optimize the system's resolution capability. Structure and method are also provided for digitally sampling the ultrasound energy which is received and for thereafter further improving the resolution of the reconstructed image of reflection by computer aided correction for refraction and attenuation of the ultrasound energy. High speed computer aided analysis also provides quantitative determinations for various acoustic parameters associated with the scanned object.

It is therefore a primary object of the present invention to provide an improved apparatus and method for ultrasound imaging.

Another primary object of the present invention is to provide an improved ultrasound imaging apparatus and method for reconstructing images of reflection by synthetically focusing ultrasound energy.

Another object of the present invention is to provide an ultrasound imaging apparatus and method for reconstructing an image of reflection from an arbitrary waveform selected so as to maximize the system's resolution capability.

Yet another object of the present invention is to improve the resolution of an image of reflection by correcting the image for distortions arising from attenuation and refraction of the ultrasound energy as it passes through the object being scanned.

Yet another object of the present invention is to provide an ultrasound imaging apparatus for improved transmission and reception of ultrasound energy waves.

Yet another object of the present invention is to provide an ultrasound imaging apparatus and method capable of providing spatial resolutions of approximately one-half wavelength in static media such as body tissues.

These and other objects and features of the present invention will become more fully apparent from the following description and appended claims taken in conjunction with the accompanying drawings.

DETAILED DESCRIPTION OF THE PREFERRED EMBODIMENTS

Reference is now made to the figures wherein like parts are designated with like numerals throughout.

1. General

Figure 1:
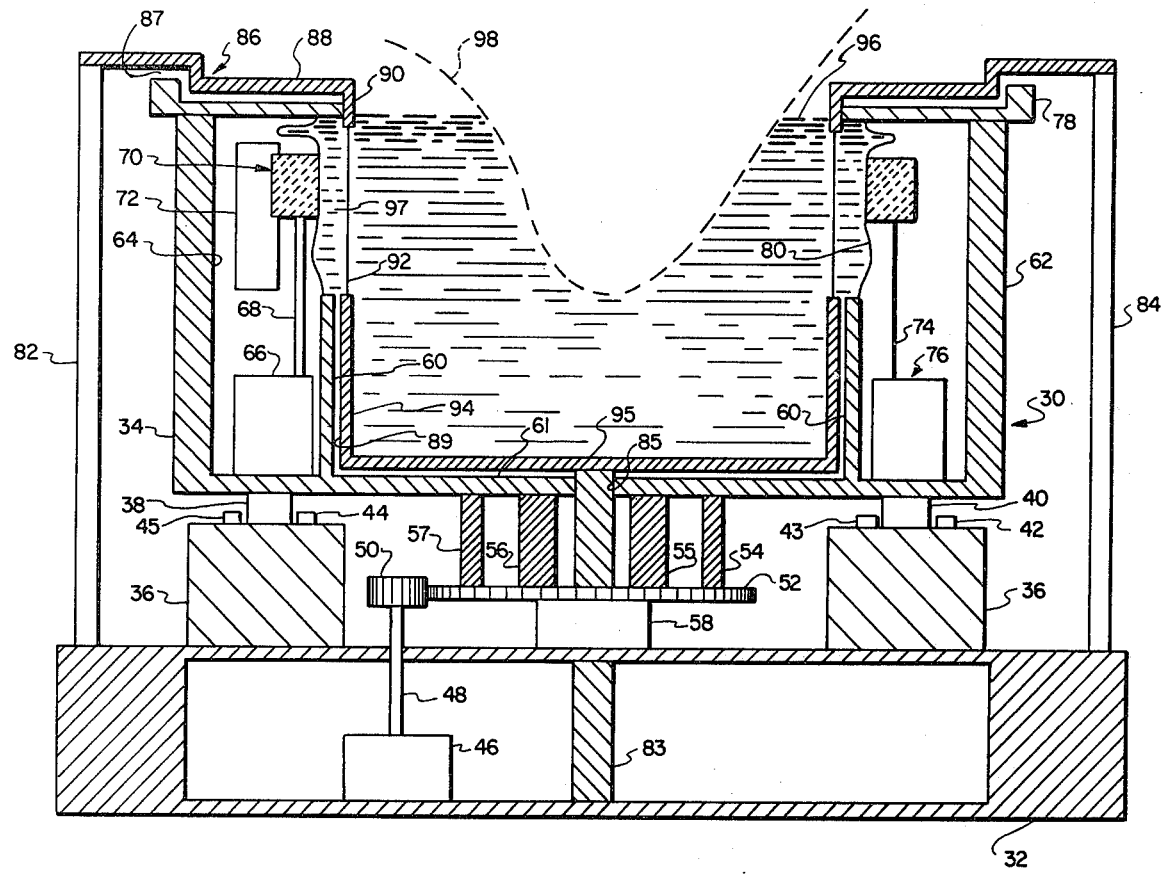
FIG. 1 is a side elevational view shown partially in cross section and schematically illustrates the ultrasound scanning apparatus of the present invention.

Reference is first made to FIG. 1 which generally illustrates the ultrasound scanning apparatus of the present invention. As shown in FIG. 1, the ultrasound scanning apparatus generally designated 30 consists of a fixed base 32 on which is rotatably mounted a movable carriage base 34. A cylindrical pedestal 36 is supported by the fixed base 32. Wheels 38 and 40 are attached to the underside of the movable carriage base 34. Small shoulders 42–45 formed on the upper surface of cylindrical pedestal 36 define a track along which the wheels 38 and 40 are guided.

A stepping motor 46 mounted within the fixed base 32 is joined by a shaft 48 to a small pinion gear 50. Pinion gear 50 engages a large drive gear 52. Pillars 54–57 are rigidly joined at one end to the top of drive gear 52 and at the opposite end to the underside of movable carriage base 34. Bearing block 58 supports drive gear 52 and movable carriage base 34.

Stepping motor 46 may be operated to turn the drive gear 52 which in turn will cause the movable carriage base 34 to rotate on top of the cylindrical pillar 36 within the tracks defined by shoulders 42–45. As hereinafter more fully described, rotation of the movable carriage base 34 may be employed to insure that an object is fully scanned from every possible angle.

With continued reference to FIG. 1, it will be seen that movable carriage base 34 has an inner cylindrical wall 60. The outer wall 62 and inner cylindrical wall 60 of movable carriage base 34 define a generally cylindrical chamber 64. Vertical drive motor 66 is mounted within chamber 64 and is connected by a shaft 68 to a circular ring of transducer arrays generally designated 70. Vertical drive motor 66 permits the circular ring of transducer arrays 70 to be vertically adjusted. Slide bracket 72 is mounted within the chamber 64 and serves to slidably guide the ring of transducer arrays 70 when it is vertically adjusted.

The ring of transducer arrays 70 is electrically connected through line 74 to an electronic circuit generally designated 76 which is also mounted within the cylindrical chamber 64 of the movable carriage base 34. As hereinafter more fully described, the electronic circuit 76 is used to transmit and receive ultrasound signals and to thereafter process the received signals so as to enable reconstruction therefrom of an image of reflection of the object being scanned.

Circular bracket 78 is attached to the top of the outer wall 62 of movable carriage base 34. A flexible, transparent window 80 extends between circular bracket 78 and the inner cylindrical wall 60 so as to enclose the transducer arrays 70, stepping motor 66 and electronic circuitry 76 within the chamber 64. The length of flexible window 80 is greater than the distance between bracket 78 and inner cylindrical wall 60. Window 80 thus serves as a flexible yet water-tight seal which permits verticle motion of the transducer arrays 70. Transparent window 80 may be made of any suitable material such as plastic or rubber.

A stationary water tank generally designated 86 is adapted to fit within the movable carriage base 34. Water tank 86 consists of a fixed top plate 88 rigidly attached to vertical support bars 82 and 84. Support bars 82 and 84 are mounted on the fixed base 32. The length of support bars 82 and 84 is chosen such that the fixed top plate 88 of water tank 86 will be slightly suspended above the bracket 78 of movable carriage 34. Thus, a space 87 is provided between bracket 78 and fixed top plate 88. Additionally, space 89 will be provided between side 94 and bottom 95 of water tank 86 and cylindrical wall 60 and bottom 61 of movable carriage 34. A third support bar 83 extends through a central hole (not shown) provided in block 58 and drive gear 52. Support bar 83 also extends through a watertight opening 85 provided in the bottom 61 of movable carriage 34. Support bar 83 thus helps to support water tank 86 in spaced relation from movable carriage 34. Since water tank 86 is suspended in spaced relation from movable carriage base 34, water tank 86 will remain stationary as movable carriage 34 is rotated. As hereinafter more fully described, rotation of the carriage 34 permits the transducer arrays 70 to scan the object 98 from every possible position around the object 98.

Fixed top plate 88 has a short downwardly extending lip 90 which extends over the end of circular bracket 78. A rubber covered window 92 extends between the lip 90 and side 94 of the water tank. Window 92 encloses within space 89, water 97 or some other suitable ultrasound medium so as to acoustically couple the transducer array 70 to the water 96 contained in tank 86. The rubber covered window 92 also permits ultrasound energy signals to be transmitted therethrough by the transducer arrays 70 and insures that the patient will be protected in the event window 92 should be broken.

Those of ordinary skill in the art will readily recognize that the ultrasound scanning apparatus generally described above may be successfully employed to scan various objects or parts of the human anatomy, as for example a patient's breast, as illustrated at 98.

2. The Transducer Configuration

Figure 2:
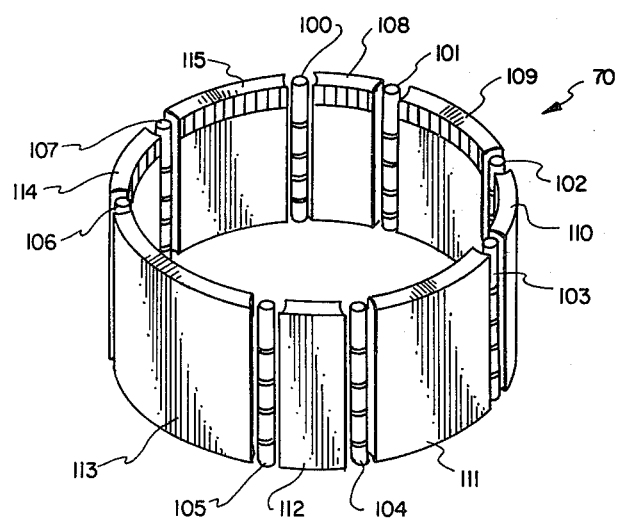
FIG. 2 is a perspective view illustrating one type of configuration which may be used for the transducer arrays employed in the ultrasound scanning apparatus of the present invention.
Figure 3:
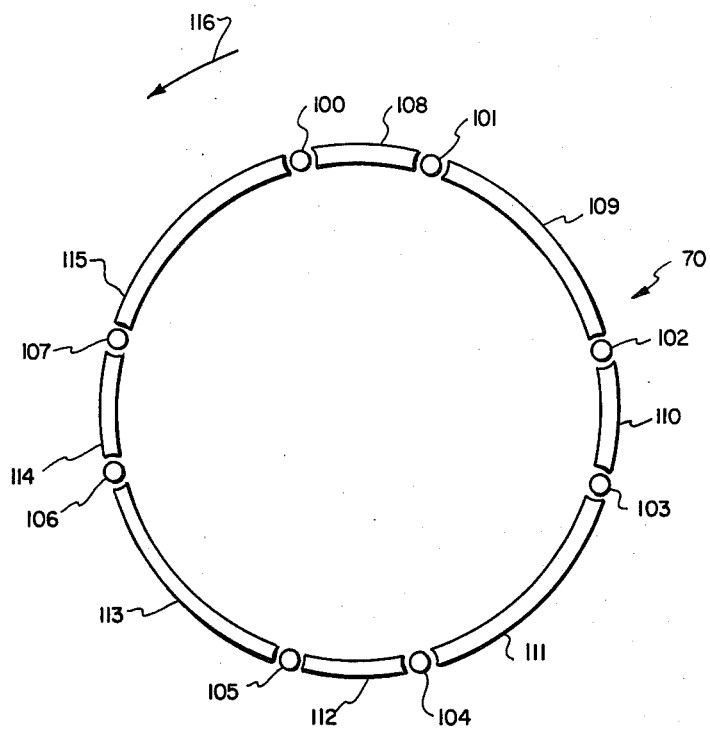
FIG. 3 is a plan view of the transducer arrays shown in FIG. 2.
Figure 4:
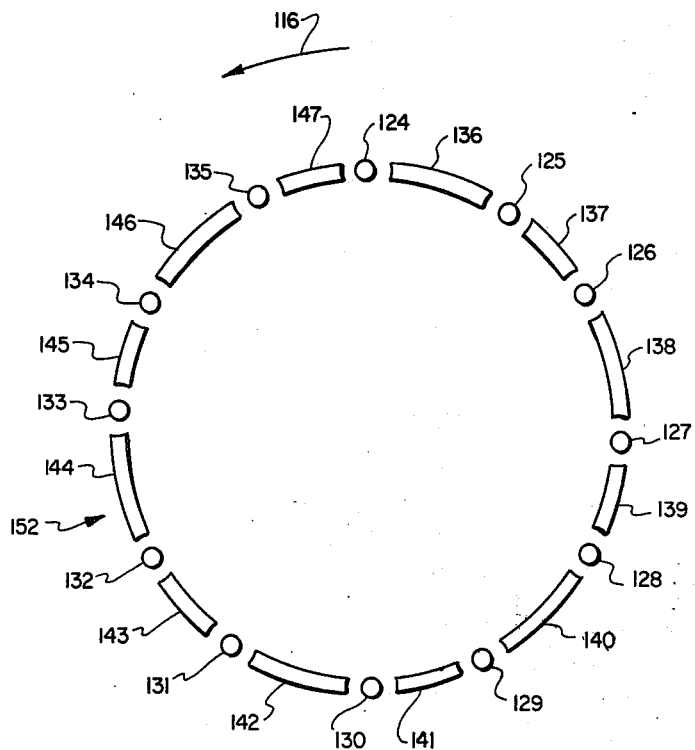
FIG. 4 is a plan view illustrating a second type of configuration for the transducer arrays of the ultrasound scanning apparatus of FIG. 1.

Reference is next made to FIGS. 2-4. FIG. 2 generally illustrates one suitable type of transducer configuration for the transducer arrays of FIG. 1. As shown in FIG. 2, the transducer configuration consists of eight transmitter arrays 100-107 and eight corresponding receiver arrays 108-115. The transmitter arrays 100-107 are thin, cylindrically shaped transducer arrays which provide point-source or line-source segment transmission of ultrasound energy signals. The receiver arrays 108-115 are arcuately shaped arrays which are interposed between each pair of transmitter arrays 100-107. For purposes hereinafter more fully described, every other receiver array (e.g. receiver arrays 108, 110, 112 and 114) has a shortened arcuate length.

Each of the transducer arrays 100-115 may be any of several well-known types of transducers. For example, transducers 100-115 may be piezoelectric type transducers which produce ultrasound energy signals directly from high frequency electrical voltages applied to the transducer. Alternatively, the transducer arrays 100-115 may be magnetostrictive type transducers having a magnetic coil (not shown) which receives the electrical oscillations and converts them into magnetic oscillations which are then applied to the magnetostrictive material to produce the desired ultrasound energy signals.

With continued reference to FIG. 2, it will be seen that the transducer arrays 100-115 are arranged to as to form a ring of arrays which encircles the object to be scanned. Significantly, by encircling the object with the transducer arrays 100-115, the arrays 100-115 may be quickly commutated by either mechanical methods, electronic methods or by both methods combined so as to completely scan the object in a much shorter time period. In the illustrated embodiment, commutation is achieved by both mechanical rotation by stepping motor 46 and by electronic triggering of transmitter arrays 100-107 in sequence, as described more fully below.

Commutation of the transmitter arrays 100-107 permits ultrasound energy to be transmitted from every possible position about the object, thus insuring that the echo data received (i.e. reflected ultrasound energy) is complete. Commutation of the receiver arrays 108-115 insures that all spaces between receiver arrays 108-115 (known as "sound holes") will be covered, thus insuring accurate collection of all ultrasound energy that is transmitted directly through the object being scanned. However, commutation of the receiver arrays 108-115 is not necessary where transmitter arrays 100-107 are also used to receive ultrasound signals. The circular ring configuration of transducer arrays 100-115 permits certain parts of the body to be scanned which would otherwise be inaccessible because of, for example, bones which might otherwise obscure the particular part of the anatomy to be scanned.

The method for commutating the arrays 100-115 is best understood by reference to FIG. 3. First, each of the transmitter arrays 100-107 is sequentially triggered so as to transmit an ultrasound energy signal. Immediately after each transmitter array 100-107 is triggered, arrays 108-115 receive ultrasound energy signals that have been either transmitted through or reflected by the object being scanned. Once this procedure has been followed for each of the transmitter arrays 100–107, the ring of arrays 70 is then mechanically rotated counterclockwise through a small angle, as designated by arrow 116. The mechanical rotation is achieved by the stepping motor 46 (see FIG. 1) which rotates the movable carriage base 34, as described above.

After rotation of the arrays 100–115 to a second position, each of the transmitter arrays 100–107 is again sequentially triggered and data is again collected through receiver arrays 108–115. This procedure is repeated until ultrasound energy has been transmitted at each possible point about the object.

Where the arrays 100–107 are used only for transmitting ultrasound energy, a second series of rotations must then be effected to cover the sound holes between each pair of receiver arrays 108–115. For example, by rotating transmitter array 101 to the position occupied by transmitter array 100, receiver arrays 109, 111, 113 and 115 will, because of their longer arcuate length, cover the spaces previously occupied by transmitter arrays 101, 103, 105 and 107. This procedure is repeated until all sound holes have been covered.

It should be noted that by increasing the number of arrays, electronic commutation may be used to reduce the angle through which the ring of transducer arrays must be rotated to achieve complete collection of both echo and transmission data. For example, as illustrated in FIG. 4, twelve transmitter arrays 124–135 are provided together with twelve receiver arrays 136–147. Again, it will be seen that every other receiver array (e.g. receiver arrays 137, 139, 141, 143, 145 and 147) has a shorter arcuate length. The increased number of transmitter arrays 124–135 together with the varying lengths for the receiver arrays 136–147 permit complete collection of echo and transmission data by rotating the ring of transducer arrays 152 through a much smaller angle than would be required for the ring of arrays 70 shown in FIGS. 2–3.

3. The Electronic Circuitry

As indicated previously in connection with FIG. 1, electronic circuitry generally designated 76 is housed within the movable carriage base 34. As hereinafter more fully described, the electronic circuitry 76 generates the ultrasound energy signals that are propagated through the object 98. The circuitry 76 thereafter detects, receives and processes the ultrasound energy signals that are reflected by and transmitted through the object 98 and then communicates the processed signals to a computer which interprets the signals and outputs the result on a visual display screen or other output device.

Of particular importance to the ultrasound scanning apparatus and method of the present invention is the provision of certain circuit components for developing a particular type of waveform for the signals from which the displayed image is reconstructed. Surprisingly high quality resolution for the reconstructed images of reflection is achieved by carefully controlling the type of waveform from which the displayed image is reconstructed, where resolution is defined as the minimal spatial separation between any two points on the reconstructed image of reflection which can be distinguished from one another.

For example, historically it has been found that for an optical instrument of diffraction aperture d and optical wavelength $\lambda$, the smallest divergence angle resolvable is approximately $0.61 \lambda/d$, otherwise known as the Rayleigh criterion. In practical terms, the limit defined by the Rayleigh criterion means that two points cannot be closer than one-half of the optical wavelength and still be capable of being resolved. Until the present invention, ultrasound scanning devices have not been capable of completely resolving two points which have been closer than about $0.6\lambda$ to $1.0\lambda$.

Significantly, resolving powers corresponding to 250 microns or less at 3 MHz (i.e. one-half wavelength) have been achieved for images of reflection reconstructed with the apparatus and method of the present invention.

Figure 5:
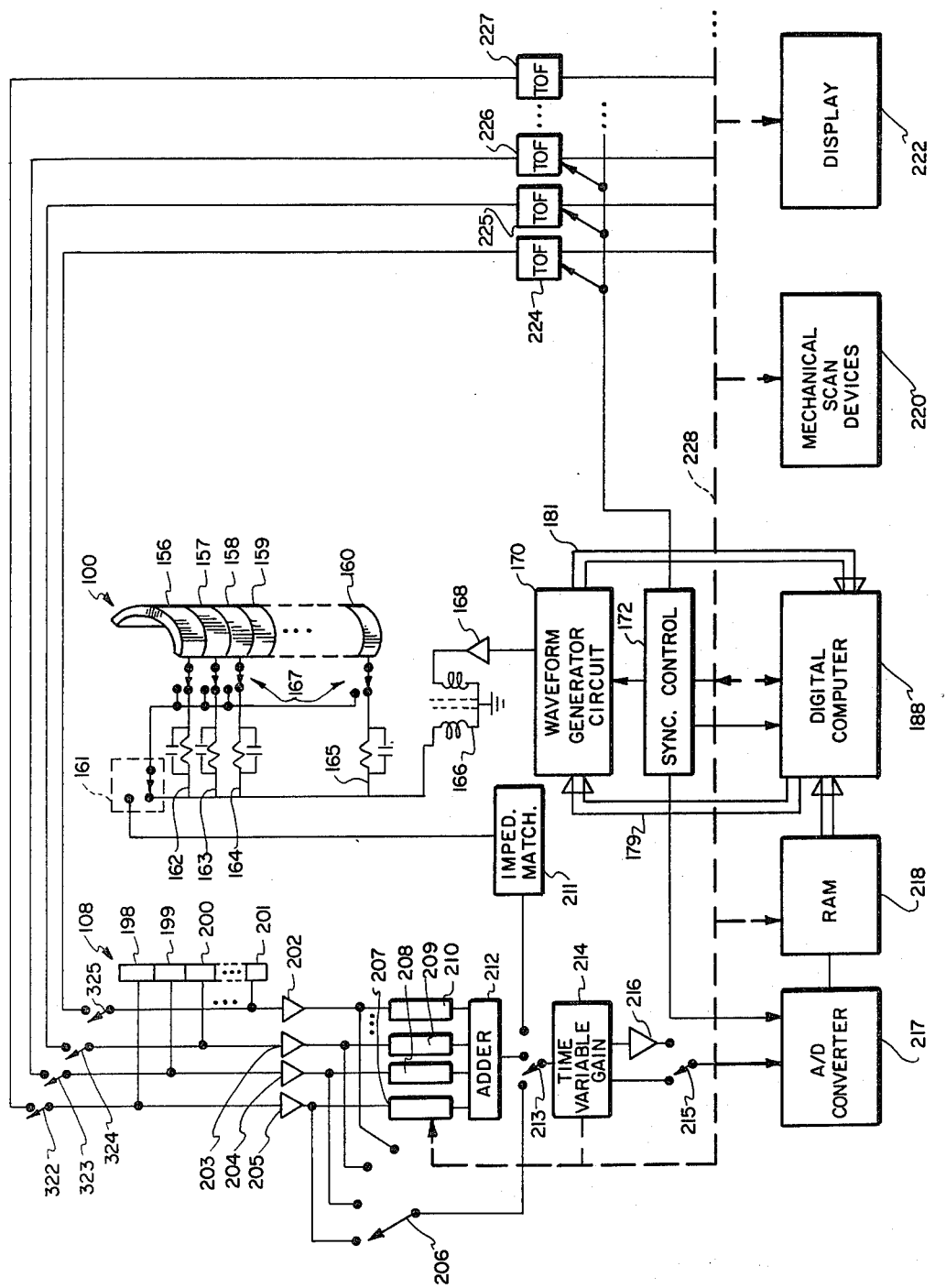
FIG. 5 is a schematic diagram illustrating one embodiment of the electronic circuitry used for transmitting and receiving ultrasound energy signals and for thereafter processing the received signals to permit reconstruction of an image of reflection for an object being scanned.

As shown in FIG. 5, each of the transducer elements 156–160 of transmitter array 100 may be electrically connected through the switches generally designated 167 to either a corresponding resistive and capacitive (RC) apodizing network 162–165, or to a transmit-receiver switch (TRSW) 161. It should be noted that each of the transmitter arrays 100–107 (see FIG. 2) are similarly connected. However, for ease of illustration only the connection for transmitter array 100 has been shown. The RC apodizing networks 162–165 are in turn connected to a transformer 166 and to one pole of TRSW 161. TRSW 161 is connected through an impedance matching network 211 to switch 213.

Transformer 166 is connected through pulse amplifier 168 to the waveform generator circuit 170. As hereinafter more fully described, waveform generator circuit 170 periodically generates a series of pulses, each pulse having the shape of a particular waveform selected as described below so as to significantly improve the resolution for the subsequently reconstructed image of reflection. Each of the pulses generated by waveform generator circuit 170 are synchronously clocked by synchronization control circuit 172 to pulse amplifier 168. Each signal pulse is then transmitted through the impedance matching transformer 166 to achieve maximum power transfer for the signals. RC apodizing networks 162–165 operate to distribute the power across the transducer array 100 by selectively varying the impedance at each transducer element 156–160. Thus, by increasing the impedance of RC networks 162 and 165 at the distal ends of array 100, the ultrasound signal transmitted by array 100 will have reduced side lobes. RC networks 162–165 could also include inductance to provide improved flexibility in reducing the side lobes.

It should also be noted that the RC networks 162–165 could be removed and the circuit of FIG. 5 could still function in essentially the same way. This is because the apodizing function provided by networks 162–165 could be programmed into the computer 188 so long as only one of the transducer elements 156–160 is used at a time to transmit. The only disadvantage to such a configuration would be to require a longer time to collect data because of the single element transmission mode employed.

Moreover, TRSW 161 and the switches generally designated 167 allow the circuit of FIG. 5 to be used in accordance with a variety of options. For example, the transducer array 100 may be used in both the transmit and receive mode, or may be used to simply transmit, depending upon the position of TRSW 161 and switches 167. With TRSW 161 in the position illustrated in FIG. 5, array 100 is ready for the transmit mode on any of the elements 156–160. Immediately after transmission from one of the elements 156–160, TRSW 161 and switches 167 may be changed to the upper poles so that all of the elements 156–160 may be used to receive the reflected signals. As hereinafter more fully described, the received signal is then passed through TRSW 161 to impedance matching network 211 and switch 213. Importantly, by multiplexing the individual transmitter array elements 156–160 in the above-described manner, improved synthetic focusing of the object will result in the vertical dimension.

Figure 6:
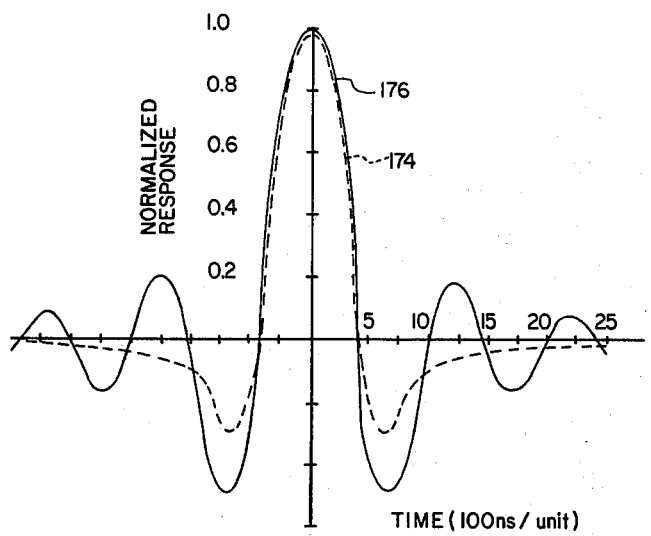
FIG. 6 is a graph illustrating two alternative types of waveforms that may be employed by the ultrasound scanning apparatus of the present invention for purposes of reconstructing an image of reflection.

FIG. 6 illustrates at 174 one suitable type of waveform developed for each signal transmitted by waveform generator circuit 170. Another suitable type of waveform that may be used advantageously in accordance with the apparatus and method of the present invention is shown at 176. Waveforms 174 and 176 are known in convolution reconstruction theory and Fourier transform theory developed in connection with X-ray computed tomographic imaging as the Tanaka-Iinuma kernel and the Ramachandran and Lakshiminaraynan kernal, respectively.

Waveform 174 is defined by the equation $$g(t, \sigma) = \frac{1}{2\pi\sigma^2}\left\{1 - \frac{t}{\sigma^2}\int_0^t \exp\left[-\frac{1}{2\sigma^2}(t^2 - s^2)\right] ds\right\}$$

where $\sigma$ corresponds to the point in time where the magnitude first reaches zero and t represents time. Waveform 176 is defined by the equation $$f(t) = \frac{2\sin(\pi t/5\beta)}{\pi t/5\beta} - \frac{\sin^2(\pi t/10\beta)}{(\pi t/10\beta)^2}$$

where $\beta$ is the point in time where the magnitude first reaches zero and t represents time. For $\sigma=2.84$ and $\beta=1$, waveforms 174 and 176 produce equal reconstruction resolution.

Figure 7:
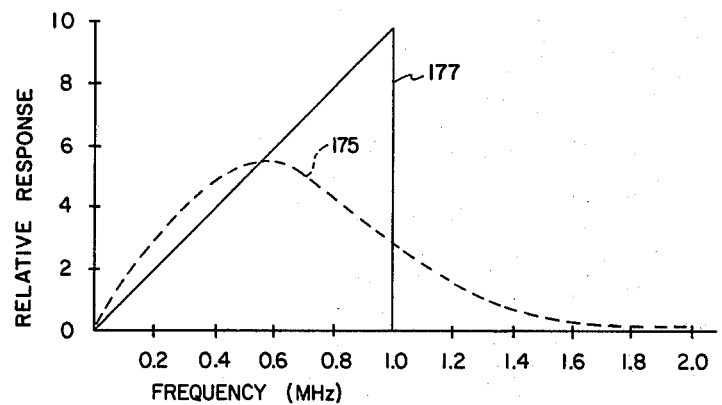
FIG. 7 is a graph illustrating the Fourier transforms for the waveforms of FIG. 6.

As can be seen from the Fourier transforms 175 and 177 (FIG. 7) which correspond to waveforms 174 and 176, the Tanaka Iinuma kernel (waveform 174) requires twice the bandwidth of waveform 176 to achieve the same resolution. However, waveform 174 has a better signal to noise ratio than waveform 176 and is thus better suited for noisy environments. Additionally, waveform 174 is better than waveform 176 for minimizing certain types of other distortions in the reconstructed image, such as concentric ring artifacts.

As more fully described below, ultrasound signals having the shape of waveforms 174 or 176 will, when combined for purposes of reconstructing an image of reflection, produce regions of both constructive and destructive interference which will significantly improve the point response of the combined signals so as to greatly enhance the resolution of the reconstructed image of reflection. Clearly, any type of waveform which is designed to improve the point response of the combined ultrasound signals in this manner could be utilized in accordance with the apparatus and method of the present invention. For example, it is possible to use waveforms that are intermediate between the waveforms 174 and 176.

Figure 8:
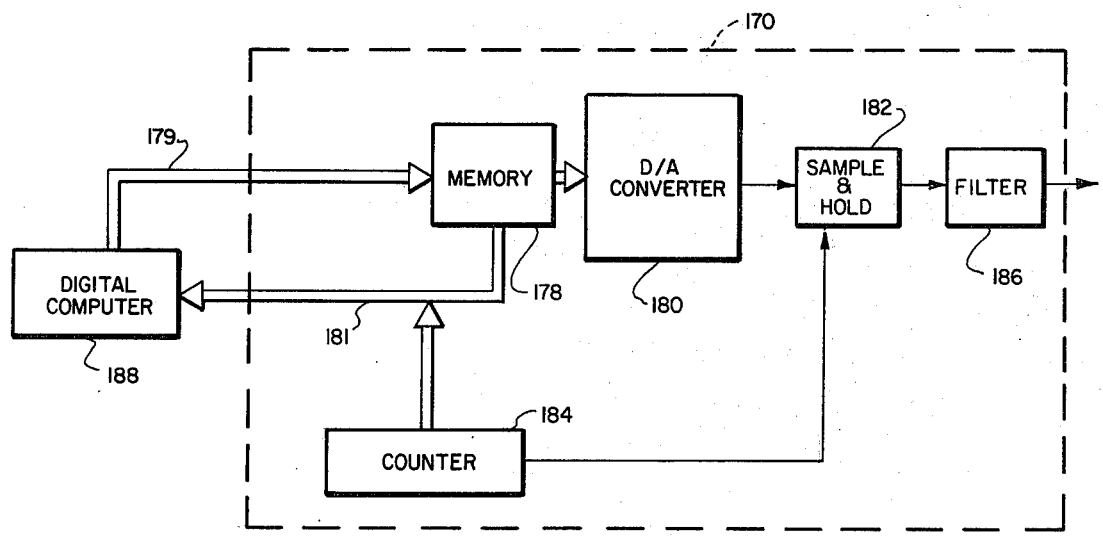
FIG. 8 is a functional block diagram illustrating the components of the waveform generator of the circuit in FIG. 5.

As shown in FIG. 8, waveform generator circuit 170 consists of five functional components. Memory circuit 178 is connected to a digital computer 188 through a read line 179 and through write line 181. Digital computer 188 may be any of several well-known types of commercially available main-frame computers or specially programmed mini-computers.

Figure 9:
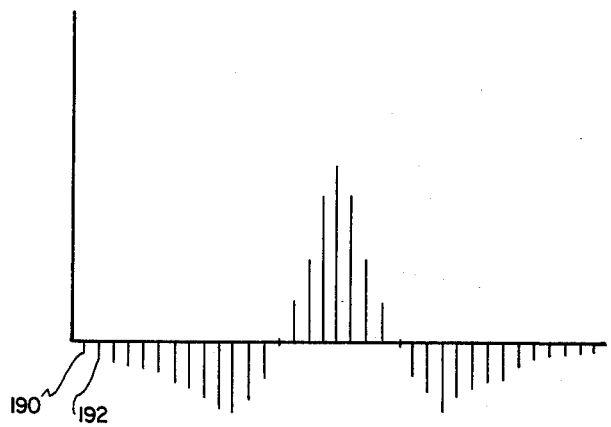
FIGS. 9, 10 and 11 are graphs illustrating the method employed by the waveform generator illustrated in FIG. 8.

Computer 188 determines the numerical value for a series of discrete points on the selected waveform, as for example waveform 174. These numerical values are stored in binary form in memory 178. Each of the discrete values stored in memory 178 is then sent to a digital-to-analog (D/A) converter 180. D/A converter 180 then transforms each of these digital values into a corresponding analog pulse, as illustrated in FIG. 9. These discrete analog pulses are then input to a sample and hold circuit 182. Sample and hold circuits such as that schematically illustrated at 182 are well known in the art and operate so as to hold each analog signal for a predetermined period of time. Counter 184 is used to control the amount of time that each signal is held by sample and hold circuit 182.

Figure 10:
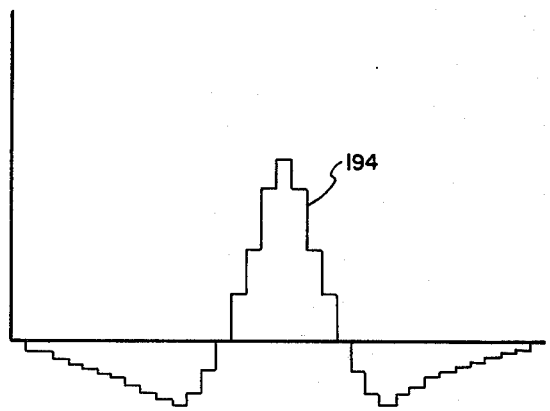
Figure 11:
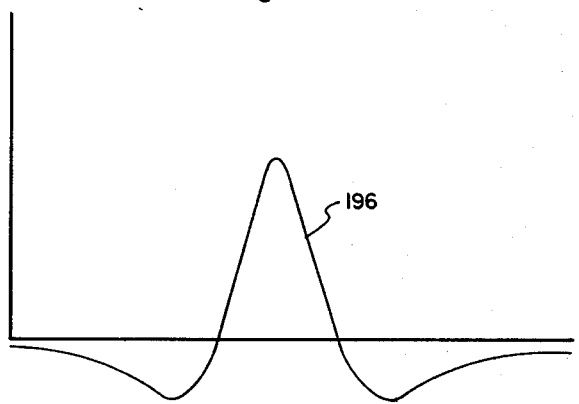

Thus, with each clock pulse from counter 184, the sample and hold circuit 182 retrieves one of the analog signals from D/A converter 180 and then holds the value of that signal for the duration of the clock pulse. For example, as illustrated in FIGS. 9 and 10, on the first clock pulse sample and hold circuit 182 will retrieve the analog pulse 190 and hold it for the duration of the clock pulse. On the next pulse analog signal 192 will be retrieved and held for the duration of the clock pulse and so on. Sample and hold circuit 182 thus outputs a waveform as illustrated at 194 in FIG. 10. Waveform 194 is then input to a low pass filter circuit 186. Low pass filter circuit 186 shapes the waveform 194 so as to output the desired signal pulse 196 illustrated in FIG. 11 which corresponds to the selected type of waveform 174.

Referring again to FIG. 5, it will be seen that each of the transducer elements 198–201 of receiving array 108 are electrically connected to one of the amplifiers 202–205. Again, it should be understood that each of the receiver arrays 108–115 (see FIG. 2) are similarly connected. However, for ease of illustration only the connection for receiver array 108 has been illustrated. Furthermore, it should also be noted that each of the transmitter arrays 100–107 may also be used to receive ultrasound energy signals, and they may also be connected in the same manner as receiver array 108. Additionally, although in the illustrated embodiment the transducer arrays 100–115 have been shown and described in a circular configuration, it will be course be appreciated that the electronic circuitry of FIG. 5 may also be employed with straight line linear transducer array configurations.

Each ultrasound signal received on one of the transducer elements 198–201 of receiver array 108 is detected and amplified by one of the amplifiers 202–205. The received ultrasound signals are then input through delay lines 207–210 to an analog adder circuit 212. Delay lines 207–210 and analog adder 212 vertically focus the received signals and thus may be used to increase the scanning system's speed by somewhat reducing the computational time needed to synthetically focus the received signals. However, the use of delay lines 207–210 and adder 212 decreases the resolution quality somewhat. Thus, delay lines 207–210 and adder 212 may be bypassed by switch 213 when desired. When delay lines 207–210 and adder 212 are bypassed by switch 213, each received signal is transmitted directly through multiplexer 206.

From the adder 212 or multiplexer 206, each received signal is then amplified by a time variable gain circuit 214. Time variable gain circuit 214 compensates for signal attenuation with time and thus keeps each signal within a range that may be accurately detected by the A/D converter 217. The signals are then compressed by a logarithmic amplifier 216 to reduce the storage space required for each signal after it is digitized by A/D converter 217. If desired, logarithmic amplifier 216 may precede the time variable gain circuit 214. Alternatively, amplifier 216 may be bypassed by switch 215.

A/D converter 217 digitizes each received ultrasound signal by converting it to a series of corresponding digital signals which are then stored in the random access memory (RAM) circuit 218. As hereinafter more fully described, digital computer 188 subsequently retrieves and interprets the signals stored in RAM 218 so as to reconstruct therefrom an image of reflection for the scanned object. The reconstructed image is then output on a display device 222 such as the screen of a CRT terminal or other suitable device.

In addition to carefully controlling the type of waveform from which the image of reflection is reconstructed, the ultrasound imaging apparatus of the present invention also improves the resolution quality for the reconstructed image of reflection by correcting the reconstructed image so as to eliminate distortions arising from attenuation and refraction of the transmitted ultrasound signals through the scanned object. As further illustrated in FIG. 5, each of the transducer elements 198–201 of the receiver array 108 is connected through one of the switches 322–325 to a corresponding time of flight detector 224–227. Time of flight detectors 224–227 determine the time it takes for the transmitted ultrasound energy signals to travel through the object being scanned. Alternatively, detectors 224–227 could be used to detect phase and amplitude.

Detectors 224–227 are switched so that only the receiver arrays directly across from the transmitter array being triggered will be used to detect the time of flight, thus eliminating reflected signals. For example, receiver arrays 111–113 are connected to the time of flight detectors when transmitter 100 (see FIG. 2) is triggered.

The synchronization control circuit 172 gates the time of flight data from detectors 224–227 through data bus 228 to the digital computer 188. As hereinafter more fully described, computer 188 uses the echo and time of flight data (or phase and amplitude data) to determine the refractive index and linear attenuation coefficient for the object being scanned. Computer 188 then determines the connecting ray between each point of the object and each of the transducer elements of the arrays. Data sampling times for each point in the reconstructed image are then corrected for refraction by computer aided integration of the object's refractive index along each connecting ray. Correction of the data for amplitude attenuation is similarly obtained by computer aided integration of the object's linear attenuation coefficient along the connecting rays.

Figure 12:
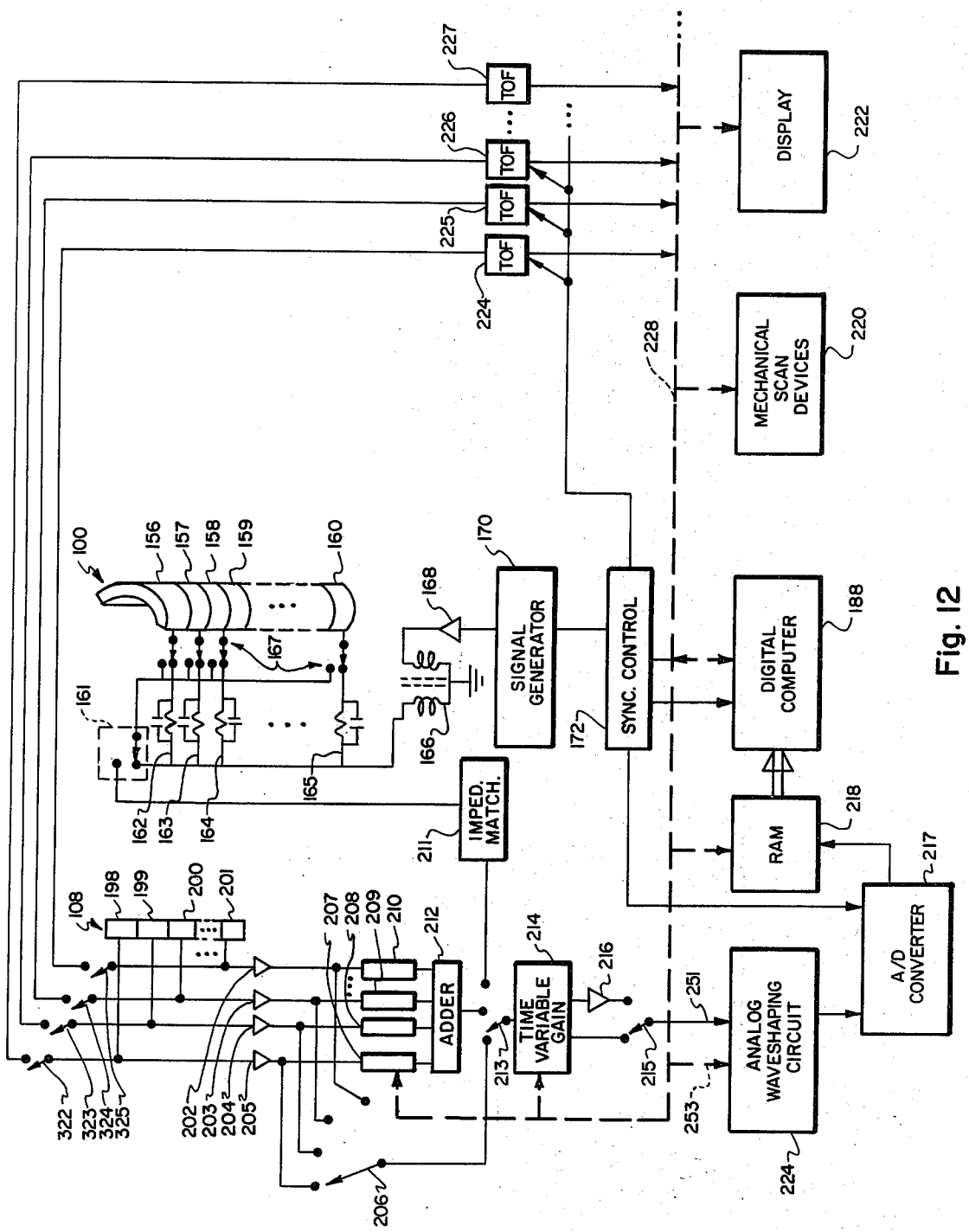
FIG. 12 is a schematic diagram illustrating a second embodiment of the electronic circuitry used for transmitting and receiving ultrasound energy signals and for thereafter processing the received signals to permit reconstruction of an image of reflection of a scanned object.

The electronic circuitry illustrated in FIG. 12 is essentially the same as that described previously in connection with FIG. 5 except for the manner in which the electronic circuitry develops the particular type of optimal waveform, as for example waveform 174, for each of the signals from which the image of reflection is reconstructed. As shown in FIG. 12, rather than developing the waveform 174 during the transmission mode, an analog waveshaping circuit 224 is used to process the ultrasound signals after they have been received so as to develop for each signal the desired waveform 174.

Figure 13:
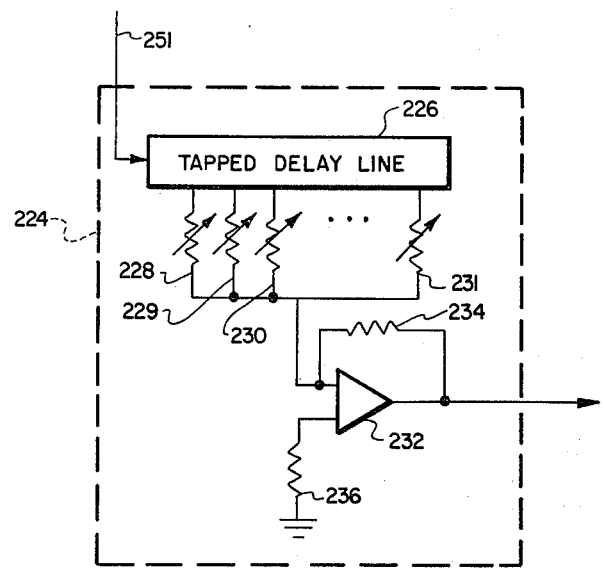
FIG. 13 is a schematic diagram illustrating one type of analog waveshaping circuit which may be employed with the electronic circuitry shown in FIG. 12.

FIG. 13 illustrates one type of circuit that may be used for the analog waveshaping circuit 224. As each ultrasound signal is received by transducer elements 198–201 (see FIG. 12), the signal is transmitted to a tapped delay line 226 (FIG. 13). Each tap of the delay line 226 is selectively weighted by a variable resistor 228–231. The weights for each of the taps of the delay line 226 are selected so that each portion of the signal which is accessed through the various taps of the delay line 226 will be multiplied by a value which corresponds to a discrete value on the waveform 174. Each portion of the signal which is thus multiplied is input through one of the terminals of the integrating amplifier 232. Resistors 234 and 236 are selected so that the appropriate biasing and integrating characteristics are achieved for the output of the amplifier 232. Additionally, it should be noted that although any suitable number of taps may be used for the delay line 226, increasing the number of taps will result in a waveform which more nearly corresponds to the desired waveform 174.

As integrating amplifier 232 sums the signals input from variable resistors 228–231, the desired waveform 174 will be output by amplifier 232. In this manner, each received ultrasound signal is convolved with the waveform 174 so as to develop for each signal a particular waveform having the shape of waveform 174. As described more fully below, when these signals are combined so as to reconstruct an image of reflection, the point response for the combined signals will be significantly improved so as to greatly enhance the quality of resolution of the image. As previously described, each such signal having the form of waveform 174 is then transmitted to the A/D converter 217 and RAM circuit 218.

Figure 14:
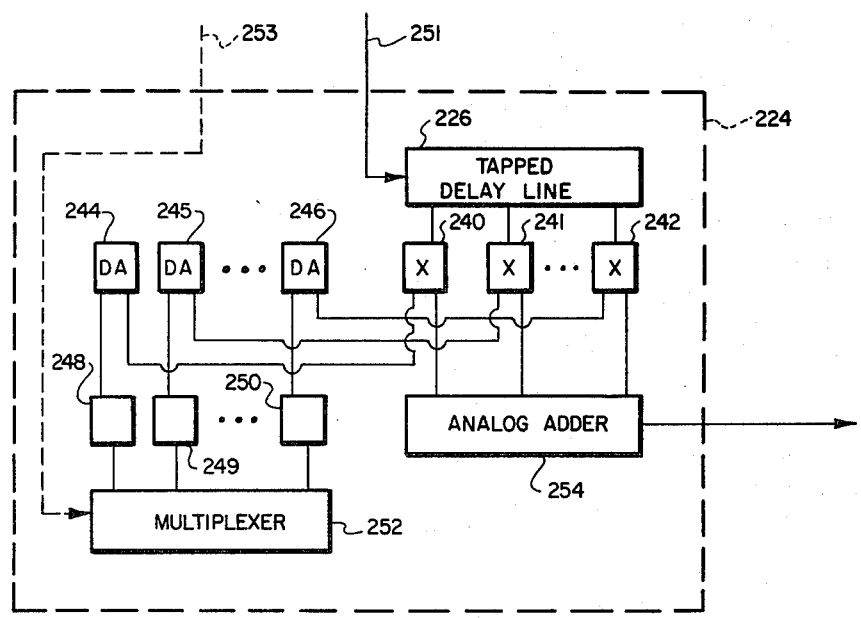
FIG. 14 is a functional block diagram illustrating a second type of analog waveshaping circuit which may be employed with the electronic circuitry of FIG. 12.

FIG. 14 illustrates a second type of circuit which may be used as the analog waveshaping circuit 224. As shown in FIG. 14, each of the taps of the delay line 226 is connected to a multiplier circuit 240–242. The multiplier circuits 240–242 are in turn connected to D/A converter circuits 244–246. The D/A converter circuits 244–246 are each connected to one of the latching circuits 248–250 which in turn are selectively accessed by a multiplexer 252.

Multiplexer 252 is connected through line 253 to the data bus 228. The digital computer 188 is used to calculate the tap weight values by which each portion of the signal received by delay line 226 is to be multiplied. The various tap weights are then transmitted through line 253 to multiplexer 252. Multiplexer 252 in turn selectively accesses the appropriate latching circuit 248–250. The particular tap weight from multiplexer 252 is then converted to an analog signal by one of the D/A circuits 244–246 and input to one of the corresponding multiplier circuits 240–242. In this manner the signal received by delay line 226 is broken down into various portions, each of which is multiplied by a tap weight value which corresponds to a discrete value on the waveforms 174.

As each portion of the signal is gated through the multiplier circuits 240–242 and multiplied, the analog adder circuit 254 sums the variously multiplied portions of the signal so as to develop therefrom the particular type of waveform 174 for each signal from which the image of reflection is to be reconstructed. Each signal which has thus been convolved with waveform 174 is then transmitted to the A/D converter 217 and RAM circuit 218.

Figure 15:
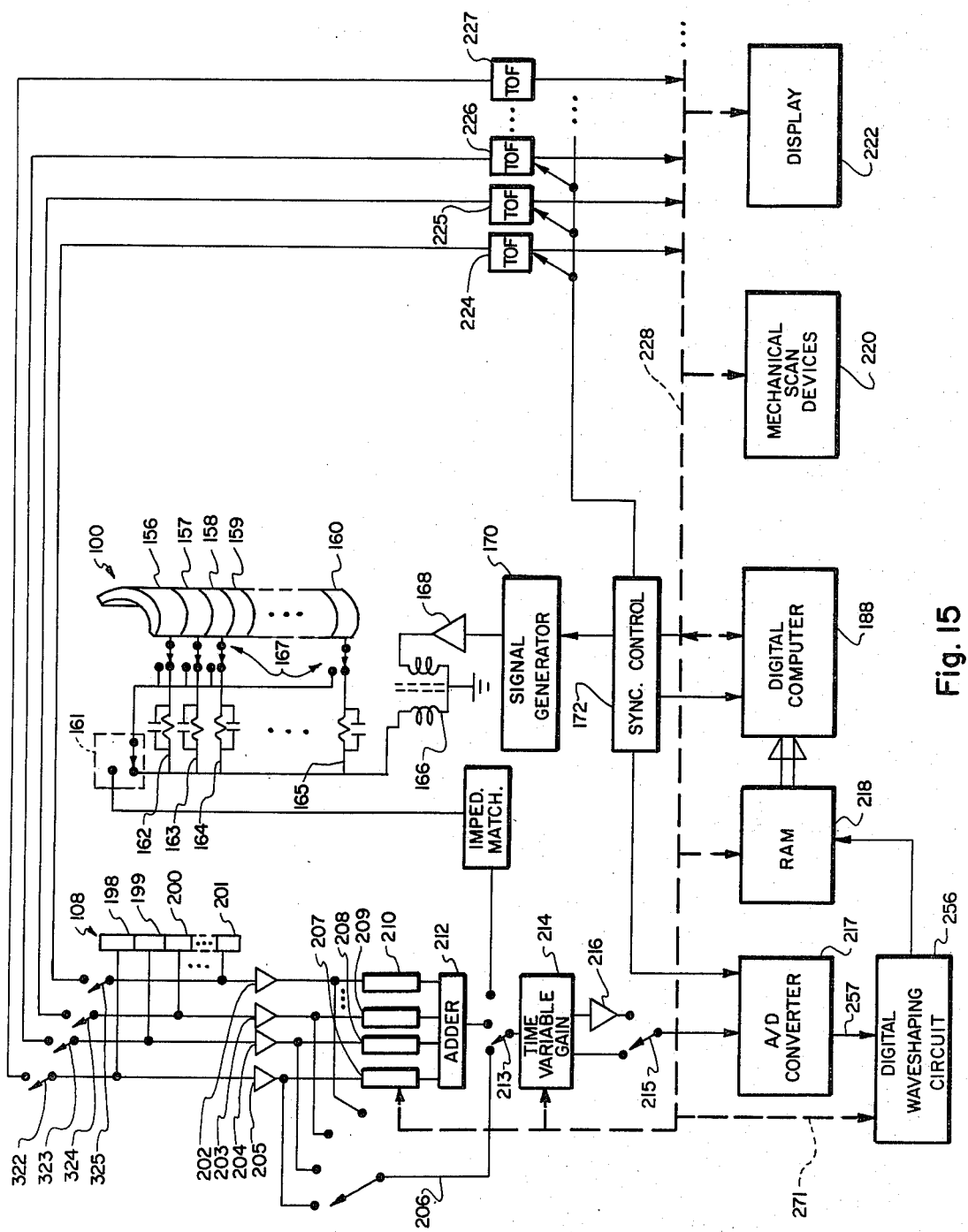
FIG. 15 is a schematic diagram of a third embodiment of the electronic circuitry for transmitting and receiving ultrasound energy signals and for thereafter processing the received signals to enable reconstruction of an image of reflection.

The electronic circuit in FIG. 15 is essentially the same as that described previously in connection with FIG. 12 except that the various ultrasound signals are processed through a digital waveshaping circuit 256 rather than being processed by an analog waveshaping circuit. As illustrated in FIG. 15, the digital waveshaping circuit 256 is connected between the A/D converter 217 and RAM circuit 218.

Figure 16:
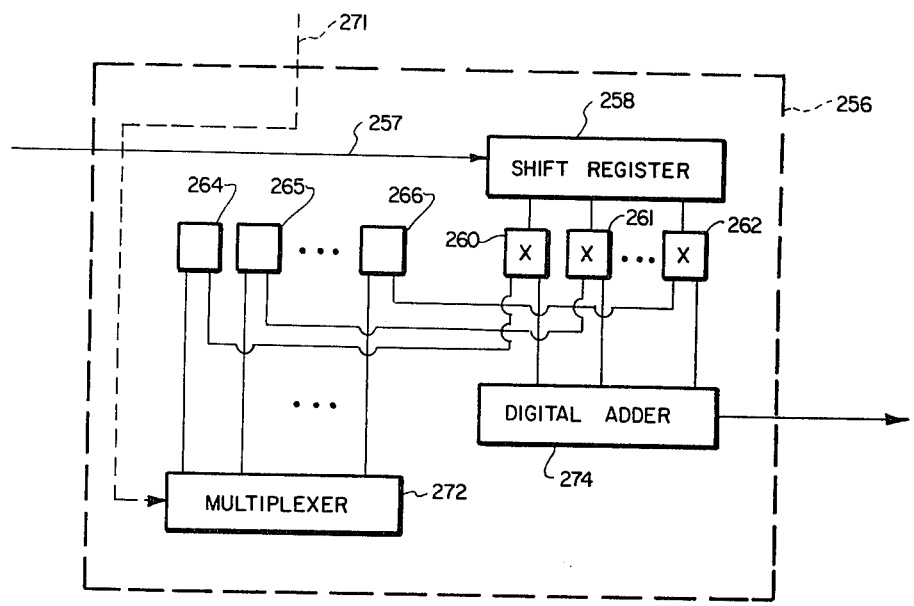
FIG. 16 is a functional block diagram illustrating one type of digital waveshaping circuitry used in conjunction with the circuit of FIG. 15.

FIG. 16 illustrates one type of circuit that may be used for the digital waveshaping circuit 256. As shown in FIG. 16, a series of digital signals corresponding to each received ultrasound signal is transmitted from the A/D converter 217 (see FIG. 15) through line 257 to a shift register 258. Each digital signal is in turn selectively accessed by a multiplier circuit 260-262. Again, any selected number of multiplier circuits 260-262 may be used. Each of the multiplier circuits 260-262 is connected to one of the latching circuits 264-266. Latching circuits 264-266 are in turn accessed through multiplexer 272. Multiplexer 272 receives from the digital computer 188 (see FIG. 15) the various values by which the multiplier circuits 260-262 are to multiply the digital signals stored in shift register 258.

Each value used to multiply the digital signals corresponds to a discrete value on the selected waveform, as for example waveform 174 (FIG. 6). Thus, as each latching circuit 264-266 is accessed by multiplexer 272, one of the digital signals stored in shift register 258 will be gated through the corresponding multiplier circuit 260-262 and input into the digital adder circuit 274. Digital adder circuit 274 then sums the digital signals which have been multiplied so as to develop from this process of convolution a series of digital signals corresponding to the desired waveform 174. The digital signals are then stored in RAM 218.

Figure 17:
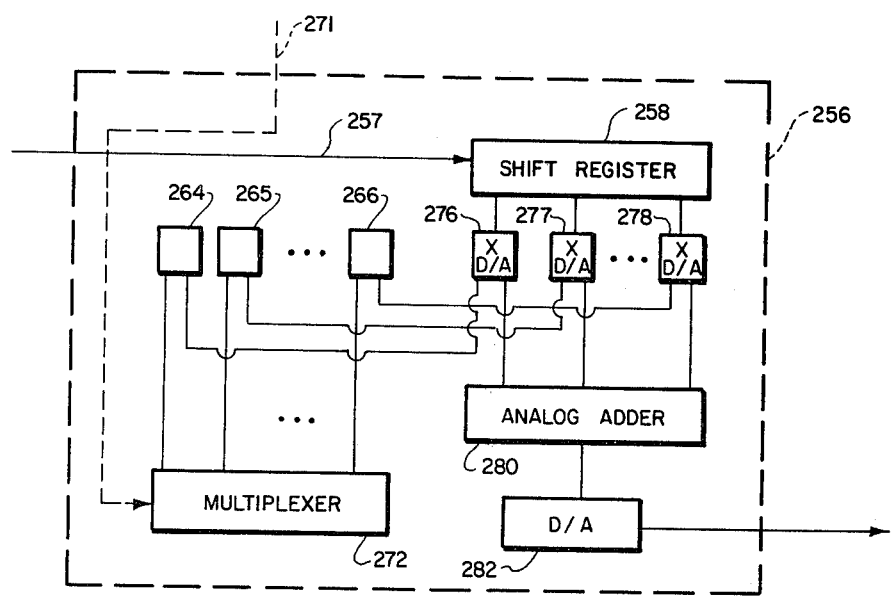
FIG. 17 is a functional block diagram illustrating a second type of digital waveshaping circuit which may be used with the circuitry of FIG. 15.

FIG. 17 illustrates a second circuit which may be used as a digital waveshaping circuit 256. The circuit of FIG. 17 differs from the circuit of FIG. 16 in that the multiplier circuits 276-278 are multiplying digital to analog circuits. Thus, as each digital signal is gated through the multiplying digital to analog circuits 276-278, the signals are multiplied and converted to analog signals. The analog signals are then added by an analog adder 280 so as to develop therefrom the particular type of waveform 174. The desired waveform is then transmitted to digital-to-analog converter 282 which transforms the waveform into a series of corresponding digital signals which are stored in RAM 218.

Figure 23:
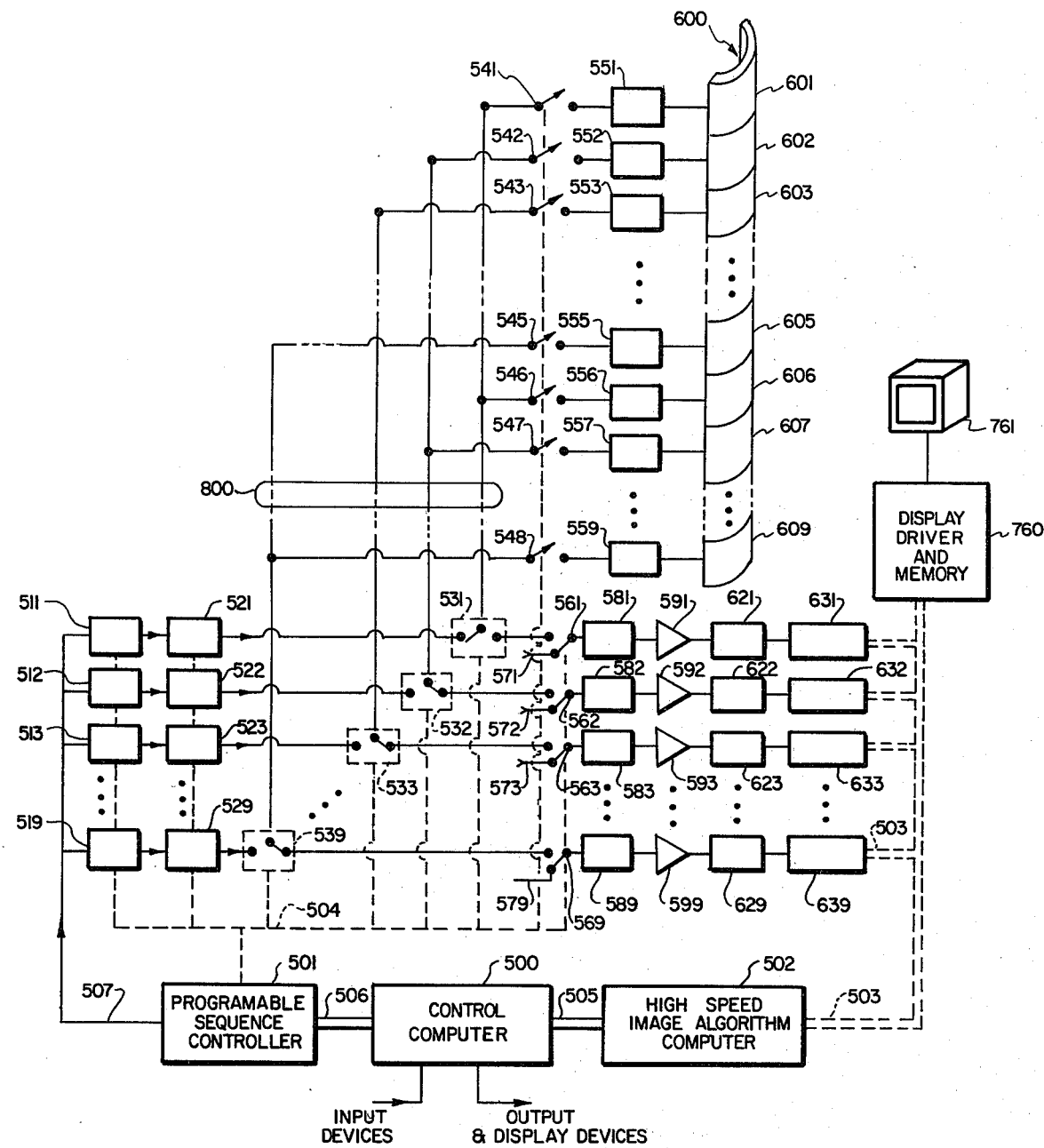
FIG. 23 is a schematic diagram of a fourth embodiment of the apparatus of the present invention.

FIG. 23 illustrates yet another embodiment of the apparatus and method of the present invention. The embodiment illustrated in FIG. 23 is designed to provide for flexible and high speed transmission and collection of data and data processing to produce the desired images of the scanned object.

The central component of the apparatus illustrated in FIG. 23 is the control computer 500. Control computer 500 is programmed to control the transmission of ultrasound pulses, data collection and subsequent data processing to produce a desired image. Control computer 500 is supplemented by two auxiliary computers 501 and 502. The auxiliary computers 501 and 502 are programmed to relieve the main computer 500 of all tasks except for high level supervision, such as input of commands or output of data. Auxiliary computer 501 is a programmable sequence controller that controls the triggering of ultrasound pulses and the opening and closing of signal path routing switches and multiplexers, as hereinafter more fully described. Auxiliary computer 502 is a special purpose computer that is programmed to process the data at high speeds and to compute the ultrasound images from the processed data.

Buss 505 is wide, high speed buss that connects the control computer 500 to the auxiliary computer 502. Buss 506 is a high speed buss connecting control computer 500 to auxiliary computer 501. Buss 503 is a very high speed, very wide buss which connects the auxiliary computer 502 to multiple random access memories (RAMs) 631-639 and to the display driver 760 and display terminal 761. The special purpose auxiliary computer 502 in combination with the high speed busses 505 and 503 and high speed RAMs 631-639 may be capable of computing images up to 100 times per second.

The operation of the circuitry illustrated in FIG. 23 begins with the programmable sequence controller 501 which is coupled through a buss 507 to a set of delayed trigger pulse generators 511-519. Delayed trigger pulse generators 511-519 are in turn coupled to waveform generator circuits 521-529. As described above in connection with the preceding embodiments of the apparatus of the present invention, waveform generator circuits 521-529 are each used to generate the particular waveform such as that illustrated at 174 or 176 in FIG. 6 so as to provide the best possible net waveform synthesis of the wave that is transmitted from the transducer element 600. In the alternative, as also described previously, the particular type of optimal waveform could be generated during the receive mode rather than the transmission mode through the use of appropriate waveshaping circuitry.

The delayed trigger pulse generators 511-519 and the waveform generator circuits 521-529 are controlled by the programmable sequence controller 501 through buss 504. Waveform generator circuits 521-529 may be constructed in accordance with the waveform generator circuit 170 previously described or in connection with FIG. 8.

The selected waveforms generated by circuits 521-529 are fed to the proper transducer array and array element, as for example transducer array 600 and transducer elements 601-609, by means of transmit-receive switches (TRSWs) 531-539 which are coupled to the array elements 601-609 through parallel lines of buss 800. TRSWs 531-539 in combination with the array element select switches 541-549 are controlled through buss 504 from programmable sequence controller 501 so that the array elements 601-609 may be multiplexed in the transmit mode so as to improve the synthetic focusing in the vertical dimension. Impedance matching networks 551-559 are used to distribute the power across transducer array 600 by selectively varying the impedance at each transducer element 601-609.

In the receive mode TRSWs 551-559 are used to connect the array elements 601-609 through the various lines of buss 800 to the impedance matching networks 581-589, which are in turn connected to time variable gain amplifiers 591-599, and analog to digital converters 621-629. The time variable gain circuits 591-599 compensate for signal attenuation with time and thus maintain each signal within a range that may be accurately detected by the analog to digital converters 621-629.

The signals are then stored in the high speed random access memories 631-639 for processing and display by the high speed auxiliary computer 502, display drive 760 and display terminal 761. The switches 561-569 permit the impedance matching networks 581-589, the time variable gain amplifiers 591-599, the analog to digital converters 621-629 and the random access memories 631-639 to be coupled to any of the transducer arrays during the receive mode, including the arrays which are used to transmit the ultrasound signals, as for example array 600.

The embodiment of the apparatus illustrated in FIG. 23 is flexible enough to accommodate two dimensional arrays for transmission, for reception of transmission data and for reception of reflection data, and thus simply represents a more general case of the embodiments which have heretofore been described.

4. The Method of Image Reconstruction

In order to synthetically focus ultrasound energy so as to reconstruct an image of reflection of an object which has been scanned by the apparatus of the present invention, it is first necessary to develop a complete set of ultrasound signals which have been reflected and transmitted through the object being scanned. As previously described, this is accomplished by encircling the object 98 (see FIG. 1) with a ring of transducer arrays 70 (see also FIGS. 2-4). Each transmitter array 100-107 is sequentially triggered in a first position so as to propagate a series of ultrasound signals through the object 98. Additionally, each element of each array, as for example elements 156-160 (see FIG. 5) of array 100, may be sequentially triggered so as to provide improved synthetic focusing in the vertical dimension.

After each transmitter array 100-107 is triggered, receiver arrays 108-115 are used to receive the reflected and transmitted ultrasound energy signals. The ring of transducer arrays 70 is then rotated as described previously to a second position and the process is then repeated. The ring of transducer arrays 70 is rotated to as many positions as needed in order to transmit ultrasound signals from each point around the object. A second series of rotations is then effected in order to eliminate the sound holes occurring at the spaces between each pair of receiver arrays 108-115. In other words, data is transmitted and received at each position around the object 98 so as to insure a complete set of both echo and transmission data. As schematically illustrated at 220 in FIGS. 5, 12 and 15, the mechanical positioning devices for the scanner may be controlled by computer 188.

As previously indicated, although the apparatus and method of the present invention could be adapted to work with a linear array configuration, the circular array configuration described above greatly increases the speed and efficiency of the scanning process. Through the utilization of electronic commutation, the ultrasound scanning apparatus of the present invention may be operated at rates of 15 or more scans per second so as to develop real time images of reflection for the object which is being scanned.

For each received signal that is reflected by or transmitted through the object being scanned, a particular type of waveform 174 or 176 (see FIG. 6) is developed. As described above, the desired waveform 174 or 176 may be developed during the transmission mode by the waveform generator circuit 170 (see FIGS. 5 and 8). Alternatively, the ultrasound signals that are received may be subsequently convolved with the waveform 174 or 176 in an analog waveshaping circuit 224 (see FIGS. 12-14) or in a digital waveshaping circuit 256 (see FIGS. 15-17) so as to develop the desired waveform 174 or 176 for each received signal.

The desired waveform 174 or 176 may also be developed through software processing of the received signals after they have been digitized. However, the waveform generator circuit 170 or waveshaping circuits 224 or 256 shown in the illustrated embodiments are preferred over software processing techniques because they are much more rapid.

Once the desired type of waveform 174 or 176 has been developed for each transmitted or received ultrasound signal, each received signal is then converted to a series of corresponding digital signals and stored in the RAM circuit 218 (FIGS. 5, 12 and 15).

The digital signals stored in RAM circuit 218 are subsequently retrieved by the digital computer 188 and combined so as to reconstruct therefrom an image of reflection for the scanned object. The method for combining the stored signals is best understood from FIGS. 18-21.

Figure 18:
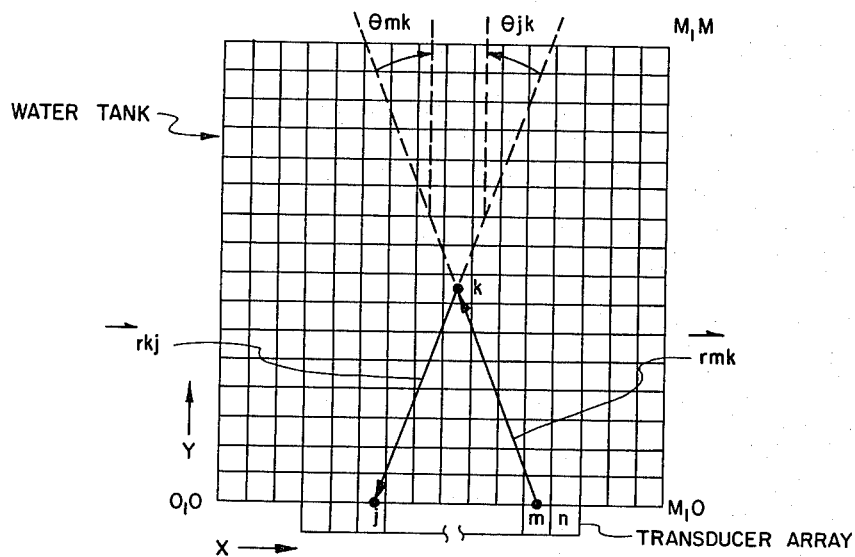
FIG. 18 is a graph from which a mathematical analysis of the apparatus and method of the present invention may be derived.

The mathematics for reconstructing an image of reflection from the received ultrasound signals may be derived by reference to FIG. 18. Let $P_k$ define a measure of the probability for acoustic amplitude scattering or reflection due to the existence of a scattering point "k" within the object being scanned. For the case of a very narrow pulse of ultrasonic energy, $P_k$ is given by the equation $$P_k = \sum_{m=1}^{n} \sum_{j=1}^{n} V(t,j,m) \, R(j,k) \, T(k,m) \tag{1}$$

where V(t, j, m) is the voltage sample at time t from the jth receiver array element when the mth transmitter array element was used as the transmitter. R(j, k) and T(k, m) are factors for correcting amplitude attenuation which occurs between the receiver element j and scattering point k and between transmitter element m and point k, respectively. R(j, k) is found from the equation $$R(j,k) = \left[ \exp\left( \int_k^j \alpha(s)ds \right) \right] \left[ \int_k^j ds \right]^q \tag{2}$$

where α is the linear attenuation coefficient measured at the center frequency of the transfer function of the system, exclusive of tissue, along the ray path $\vec{r_{kj}}$ connecting scattering point k and receiver element j, and q is a real number from 0.5 for cylindrical waves to 1.0 for spherical waves. Similarly, T(k, m) is found from the equation $$T(k,m) = \left[ \exp\left( \int_m^k \alpha(s)ds \right) \right] \left[ \int_m^k ds \right]^q \tag{3}$$

The time t in equation (1) is corrected to account for refraction of the ultrasound energy as it passes through the object. The corrected time t is found from the equation $$T = \left[ \int_m^k \frac{ds}{u(s)} + \int_k^j \frac{ds}{u(s)} \right] \frac{1}{\Delta t} \quad (4)$$

where $\Delta t$ is the sampling interval time between successive samples in the digitized signal and $1/u$ is the object's refractive index.

One suitable computer program for determining the linear attenuation coefficient and refractive index from either the detected time of flight data or the detected phase and amplitude data, and for thereafter reconstructing an image of reflection by performing the calculations for equations (1)–(4) is referenced below.

Figure 19:
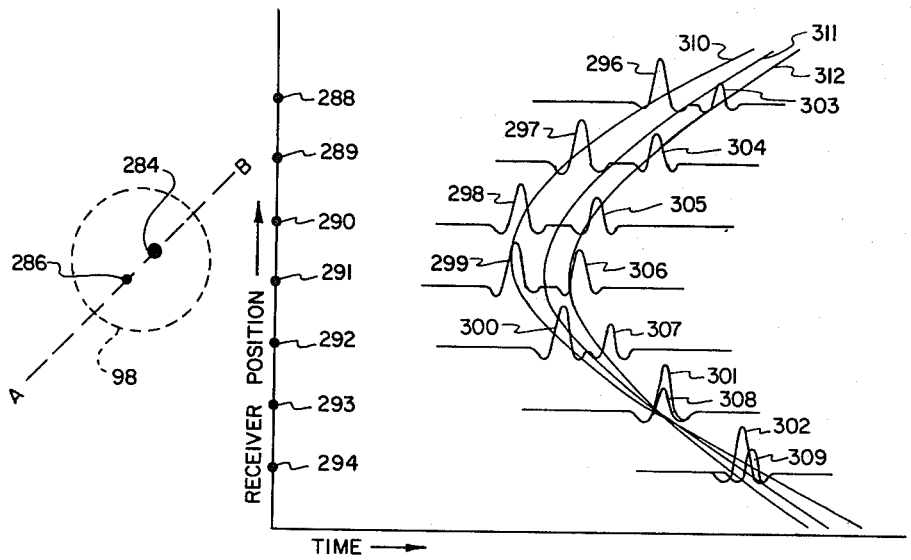
FIGS. 19–20 are graphs illustrating the effect of the waveforms of FIG. 6 on the point response of the signals from which an image of reflection is reconstructed.
Figure 20:
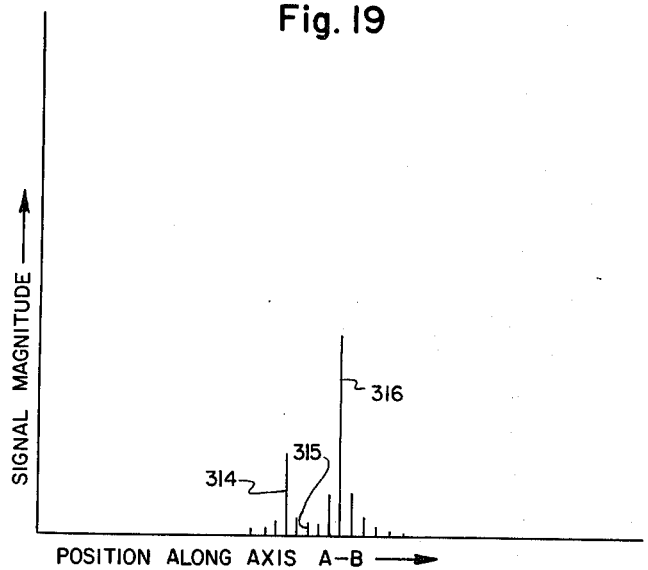
Figure 21:
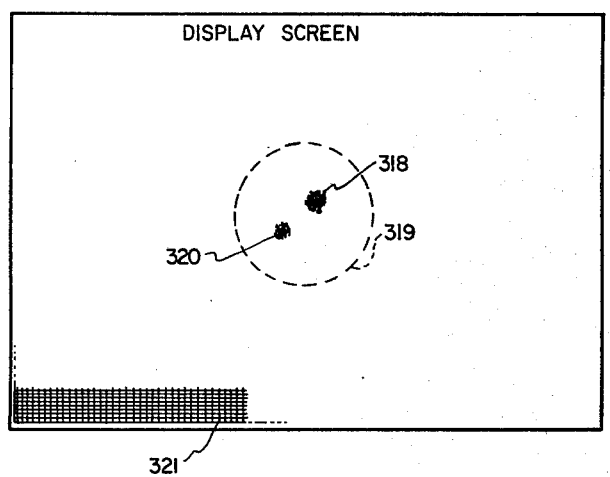
FIG. 21 is a schematic illustration of an image of reflection reconstructed from synthetically focused ultrasound energy in accordance with the apparatus and method of the present invention.

The concept which forms the basis for the abovedescribed mathematics is best understood by reference to FIGS. 19–21. For example, assume the existence of two scattering points 284 and 286 along an imaginary axis A-B within object 98, as illustrated in FIG. 19. Furthermore, assume that each of the points 288–294 represent transducer elements on a receiver array. Each of the transducer elements corresponding to the points 288–294 will detect a reflected ultrasound energy signal from the scattering points 284 and 286. For scattering point 284 a series of signals 296–302 will be detected. For the smaller scattering point 286 a series of smaller signals 303–309 will be detected.

It will be noted from FIG. 18 that the two sets of signals 296–302 and 303–309 corresponding to the scattering points 284 and 286 may be graphically located along a set of curves 310 and 312. The curves 310 and 312 graphically represent the spatial distribution which occurs as a function of time for each set of signals corresponding to a given scattering point in the object.

It can be shown that for a straight line transducer array, curves 310 and 312 will be hyperbollically shaped. For a ring of transducer arrays encircling the object, curves 310 and 312 will have a sinusoidal-like shape. Thus, for each scattering point in the object 98, a set of signals will be received which are spatially distributed along a curve that may be calculated from the physical parameters of the system.

In order to reconstruct an image of reflection from the received signals which have been subsequently processed and stored in RAM circuit 218, the computer 188 performs a line integration along each curve 310 and 312.

As shown in FIG. 21, the display screen is divided into a large number of very small picture elements such as partially illustrated at 321. For each picture element (commonly referred to as "pixel"), computer 188 assumes the existence of a corresponding scattering point in object 98 and calculates the curve along which the received signals for the assumed scattering point would be distributed. Computer 188 then accesses all address locations in RAM 218 that correspond to the signals distributed along the curve for the assumed scattering point. If a scattering point in fact is found in the object 98 which corresponds to the scattering point assumed at a given pixel on the display screen, a series of values from the waveforms of the set of received signals will be added together by computer 188 when it integrates along the corresponding curve. Otherwise, no waveform values will be added by computer 188 when it integrates along the curve.

For example, if the computer 188 assumes scattering points at the pixels which correspond to scattering points 284 and 286 in the object 98, then values from each waveform corresponding to signals 296–302 and 303–309 will be added together as computer 188 integrates along curves 310 and 312. As shown in FIG. 20, this integration by computer 188 results in a signal value at a position along axis A-B that corresponds in magnitude and location to a particular scattering point. Thus, signal 314 corresponding to scattering point 286 results from the line integration along curve 310 and signal 316 corresponding to scattering point 284 results from the line integration along curve 312. Signals 314 and 316 are subsequently used to excite corresponding pixels on the display screen (see FIG. 21) so as to produce a reconstructed image 319 having scattering points 318 and 320 which correspond in size and spatial distribution to the actual object 98 and scattering points 284 and 286 within object 98.

Figure 22:
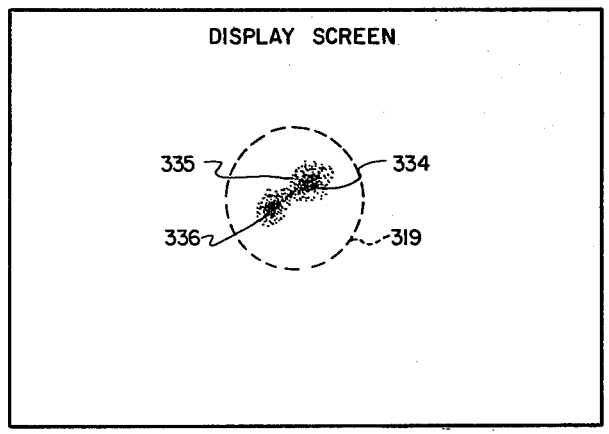
FIG. 22 is a schematic illustration of a blurred image of reflection.

As previously mentioned, one of the primary limitations which has operated to reduce the effectiveness of ultrasound scanning devices is the poor resolution that often results for the reconstructed image of reflection. As shown in FIG. 22, where the point response of the combined ultrasound signals is not well defined, the resulting image of reflection 319 will be badly blurred, as at 335, making resolution of the corresponding points 334 and 336 within the reconstructed image 319 difficult or impossible.

In contrast, it will be noted in FIGS. 20 and 21 that the point response of signals 314 and 316, derived from the line integrations of curves 310 and 312, is significantly enhanced by using a particular type of waveform 174 or 176 (see FIG. 6) for each signal 296–309. Since the waveforms 174 or 176 (see FIG. 6) have a very sharp peak at their center, integration of the curves 310 and 312 produces extreme signal values 314 and 316 at the positions along the axis A-B that correspond to actual scattering points 284 and 286. These extreme values are the result of constructive interference by the sharp center peaks of the waveforms 174 or 176 for the signals 296–302 and 303–309 situated along each curve.

Further, it will be noted that for those positions along axis A-B where no scattering point is found, the signals, as for example signal 315 (see FIG. 20), resulting from the integrations along corresponding curves, as for example curve 311 (see FIG. 19), will be at or near zero. For example, curve 311 (FIG. 19) corresponds to a position along axis A-B situated between scattering points 284 and 286 where no scattering point is found. Because curve 311 is situated so closely to curves 310 and 312, curve 311 will pass through the center peaks of some of the waveforms of the signals situated along curves 310 and 312, as for example the center peak of signal 300. However, curve 311 will also pass through the negative regions of others of the waveforms for the signals, as for example signals 302 and 309. As computer 188 integrates along curve 311, the negative values will tend to offset the positive values, thus keeping the resulting signal 315 (FIG. 20) near or at zero.

Thus, the negative portions of waveforms 174 or 176 will produce regions of destructive interference which will tend to improve the point response of the signals 314 and 316 by keeping signals at or near zero for points in the reconstructed image that do not correspond to scattering points in the object. At the same time, the sharp center peaks of waveforms 174 or 176 will produce regions of constructive interference which will tend to result in extreme signal values for points in the reconstructed image that correspond to scattering points within the object. As previously described, the improved point response for the combined signals results in a surprisingly high resolution image of reflection, as illustrated by points 318 and 320 of the reconstructed image 319 in FIG. 21.

Additionally, resolution of the reconstructed image 319 can be even further improved by readjusting the image to take into account the effect of attenuation and refraction of ultrasound signals passing through the object. Transmission data (i.e. time of flight or phase and amplitude data) and echo data (i.e. reflected ultrasound signals) are first detected by the electronic circuitry and sent to computer 188. Computer 188 then uses this data to determine the refractive index and linear attenuation coefficient for the object being scanned. Once these parameters have been determined, connecting rays between the elements of the receiver arrays and each point in the object are calculated by computer 188. The process is then repeated for the elements of the transmitter arrays.

Once the connecting rays have been obtained, data sampling times for each point in the reconstructed image are corrected for refraction by computer aided integration of the object's refractive index along each connecting ray from transmitter element to scattering point and from scattering point to receiver element. Computer 188 then interpolates to develop a corrected time address map for each point in the reconstructed image for a given transmitter and receiver pair. Similarly, the linear attenuation coefficient is integrated along each connecting ray and then computer 188 interpolates to develop an amplitude correction map for all points in the reconstructed image for a given transmitter and receiver pair. Computer 188 then causes the reconstructed image of reflection to be adjusted according to the time address and amplitude correction maps. The computer 188 then begins again for a new transmitter-receiver pair by recomputing new connecting rays and the time address and amplitude corrections are made a second time. This process may be repeated through a series of iterations until all transmitter-receiver paris are completed. The result is an image of reflection of surprisingly high resolution quality.

Computer 188 may be programmed in accordance with the foregoing description in any suitable manner that is adapted for the particular type of computer 188 used. One such suitable program listing is reproduced in full in my copending application Ser. No. 942,740, which listing is herein incorporated by reference. It should of course be recognized that the invention lies in the apparatus and method defined by the claims, and is not intended to be limited by the representative program listing incorporated above.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. An ultrasound imaging apparatus for reconstructing images of reflection from synthetically focused ultrasound energy, said apparatus comprising:

(1) a ring of transducer arrays adapted to circumscribe the object being scanned, said ring of transducer arrays comprising a plurality of transmitter arrays and receiver arrays, said transmitter arrays being located at different points around said ring of arrays;
(2) means, electronically connected to said transducer arrays, for sequentially triggering said transmitter arrays, thereby propagating semicircular wave fronts of ultrasound energy through said object at said different points around said ring of transducer arrays;
(3) means, connected to said ring of transducer arrays, for commutating said transmitter arrays so as to transmit ultrasound energy from each possible position around said object;
(4) means for sequentially triggering each individual element of each transducer array;
(5) means, electronically connected to said receiver array, for electronically storing said received ultrasound signals;
(6) means for developing a particular type of waveform for each said stored signal such that when said stored signals are combined so as to reconstruct therefrom an image of reflection, regions of both constructive and destructive interference will occur, said regions improving the point response of said combined signals so as to enhance the resolution of said reconstructed image of reflection;
(7) means, electronically connected to said storage means, for combining said stored signals so as to reconstruct therefrom said image of reflection corresponding to said scanned object; and
(8) means for displaying said reconstructed image of reflection.

2. An ultrasound imaging apparatus for reconstructing images of reflection from synthetically focused ultrasound energy, said apparatus comprising:

(1) a ring of transducer arrays adapted to circumscribe the object being scanned, said ring of transducer arrays comprising a plurality of transmitter arrays and receiver arrays, said transmitter arrays being located at different points around said ring of arrays;
(2) means, electronically connnected to said transducer arrays, for sequentially triggering said transmitter arrays, thereby propagating semicircular wave fronts of ultrasound energy through said object at said different points around said ring of transducer arrays;
(3) means, connected to said ring of transducer arrays, for commutating said transmitter arrays so as to transmit ultrasound energy from each possible position around said object;
(4) means for sequentially triggering each individual element of each transducer array;
(5) means, electronically connected to said receiver array, for electronically storing said received ultrasound signals;
(6) means, electronically connected to said receiver array, for detecting transmission data from which the refractive index and attenuation coefficient for said object may be determined;
(7) means, electronically connected to said storage means, for combining said stored signals so as to reconstruct therefrom an image of reflection corresponding to said scanned object;

(8) means, electronically connected to said detecting means, for determining the refractive index and attenuation coefficient for each point in said object;

(9) means for correcting each corresponding point of said reconstructed image of reflection in accordance with the determined point-dependent refractive index and attenuation coefficient for said object so as to eliminate distortions arising from refraction and attenuation of ultrasound energy through said object, thereby enhancing the resolution for said reconstructed image of reflection; and

(10) means for visually displaying said reconstructed image of reflection.

3. A method of reconstructing images of reflection from synthetically focused ultrasound energy comprising the steps of:

(1) encircling said object with a plurality of transmitter and receiver transducer arrays;

(2) propagating semicircular wavefronts of ultrasound energy at different points around said object by sequentially triggering a plurality of said transmitter arrays;

(3) commutating said transmitter arrays to permit transmission of ultrasound energy waves at each point around said object;

(4) sequentially triggering each individual array element of each transmitter array;

(5) receiving ultrasound energy signals that have been either reflected by or transmitted through an object being scanned;

(6) electronically storing said received ultrasound signals;

(7) developing a particular type of waveform for each said stored signal such that when said stored signals are combined so as to reconstruct therefrom an image of reflection of said object, regions of both constructive and destructive interference will occur, said regions improving the point response of said combined signals so as to enhance the resolution of said reconstructed image of reflection;

(8) electronically combining said stored signals so as to reconstruct therefrom said image of reflection corresponding to said scanned object; and (9) visually displaying said reconstructed image of reflection.

4. An improved method of reconstructing images of reflection from synthetically focused ultrasound energy comprising the steps of:

(1) encircling said object with a plurality of transmitter and receiver transducer arrays;

(2) propagating semicircular wavefronts of ultrasound energy at different points around said object by sequentially triggering a plurality of said transmitter arrays;

(3) commutating said transmitter arrays to permit transmission of ultrasound energy waves at each point around said object;

(4) sequentially triggering each individual array element of each transmitter array;

(5) receiving ultrasound energy signals that have been either reflected by or transmitted through an object being scanned;

(6) electronically storing said received ultrasound signals;

(7) detecting transmission data from which the refractive index and attenuation coefficient for said object may be determined;

(8) determining the refractive index and attenuation coefficient for each point in said object;

(9) electronically combining said stored signals so as to reconstruct therefrom an image of reflection corresponding to said scanned object;

(10) correcting each corresponding point of said reconstructed image of reflection in accordance with the determined point-dependent refractive index and attenuation coefficient for said object so as to eliminate distortions in said reconstructed image aising from refraction and attenuation of ultrasound energy through said object, thereby enhancing the resolution for said reconstructed image; and

(11) visually displaying said corrected reconstructed image of reflection.

* * * * *

UNITED STATES PATENT AND TRADEMARK OFFICE
CERTIFICATE OF CORRECTION

PATENT NO. : 4,317,369
DATED : March 2, 1982
INVENTOR(S) : Steven A. Johnson

It is certified that error appears in the above-identified patent and that said Letters Patent are hereby corrected as shown below:

Column 17, line 3 (in the equation); " T = " should read -- t = --

Column 17, line 16: "the abovede- " should read --the above de- --

Column 19, line 42: "paris are" should read --pairs are--

Column 22, line 38: "aising" should read --arising--

Signed and Sealed this

Twenty-first Day of September 1982

[SEAL]

Attest:

GERALD J. MOSSINGHOFF

Attesting Officer

Commissioner of Patents and Trademarks